United States Patent
Jang et al.

(10) Patent No.: US 11,628,195 B2
(45) Date of Patent: Apr. 18, 2023

(54) METHOD FOR PREPARING IRIDOID-RICH NONI FRUIT EXTRACT OR FRACTION THEREOF, METHOD FOR PREPARING IMMUNE-ENHANCING ACTIVE MATERIAL-RICH NONI FRUIT EXTRACT OR FRACTION THEREOF AND USE OF NONI FRUIT EXTRACT OR FRACTION THEREOF

(71) Applicants: Cosmax NBT, Inc., Seoul (KR); Cosmax NS, Inc., Seoul (KR)

(72) Inventors: Ji Hwan Jang, Gyeonggi-do (KR); Jin Hak Kim, Seoul (KR); Bo Ra Jin, Seoul (KR); Su Young Choi, Gyeonggi-do (KR); Hyun Ji Kim, Gyeonggi-do (KR)

(73) Assignees: Cosmax NBT, Inc., Seoul (KR); Cosmax NS, Inc., Seoul (KR)

( * ) Notice: Subject to any disclaimer, the term of this patent is extended or adjusted under 35 U.S.C. 154(b) by 0 days.

(21) Appl. No.: 17/257,222

(22) PCT Filed: Jun. 2, 2020

(86) PCT No.: PCT/KR2020/007155
§ 371 (c)(1),
(2) Date: Dec. 30, 2020

(87) PCT Pub. No.: WO2020/246777
PCT Pub. Date: Dec. 10, 2020

(65) Prior Publication Data
US 2022/0080018 A1    Mar. 17, 2022

(30) Foreign Application Priority Data

Jun. 3, 2019 (KR) .................. 10-2019-0065431

(51) Int. Cl.
*A61K 36/746*  (2006.01)
*A61P 37/04*   (2006.01)
*A61K 31/7048* (2006.01)

(52) U.S. Cl.
CPC ........ *A61K 36/746* (2013.01); *A61K 31/7048* (2013.01); *A61P 37/04* (2018.01); *A61K 2236/15* (2013.01); *A61K 2236/331* (2013.01); *A61K 2236/333* (2013.01); *A61K 2236/39* (2013.01); *A61K 2236/53* (2013.01)

(58) Field of Classification Search
None
See application file for complete search history.

(56) References Cited

U.S. PATENT DOCUMENTS

| 11,160,840 B2 | 12/2021 | Hwang et al. |
| 2011/0206787 A1 | 8/2011 | West et al. |
| 2020/0009208 A1 | 1/2020 | Hwang et al. |
| 2021/0401916 A1 | 12/2021 | Hwang et al. |

FOREIGN PATENT DOCUMENTS

| CN | 109198635 A * | 1/2019 |
| JP | 2013-520515 | 6/2013 |
| KR | 10-2009-0072555 | 7/2009 |
| KR | 10-1949617 | 5/2017 |
| KR | 10-2082106 | 2/2020 |

OTHER PUBLICATIONS

Murata et al., "Activation of cell-mediated immunity by Morinda citrifolia fruit extract and its constituents," Nat Prod Commun. (2014) 9(4): 445-450.
Nayak et al., "Immunostimulant activity of noni (Morinda citrifolia) on T and B lymphocytes," Pharm Biol. (2010) 48(7): 724-731.
U.S. Appl. No. 17/257,529, filed Dec. 31, 2020, by Geum et al.
U.S. Appl. No. 17/935,043, filed Sep. 23, 2022, by Geum et al.

* cited by examiner

*Primary Examiner* — Susan Hoffman
(74) *Attorney, Agent, or Firm* — Morrison Foerster LLP

(57) ABSTRACT

The present invention relates to a method of preparing a noni fruit extract containing a high iridoid content or a fraction thereof, a method of preparing a noni fruit extract containing a high content of an immune-enhancing active substance or a fraction thereof, and a use of a noni fruit extract or a fraction thereof, and more specifically, the present invention provides a method of preparing a noni fruit extract containing a high iridoid content or a fraction thereof, including preparing a noni fruit extract by using ethanol in a specific concentration range as an extraction solvent, a method of preparing a noni fruit extract containing a high content of an immune-enhancing active substance or a fraction thereof, a pharmaceutical composition for enhancing immunity including the extract or a fraction thereof, a health functional food composition including the same constitution, a method of enhancing immunity using the extract or a fraction thereof, and a use of the extract or a fraction thereof in preparation of medicine for preventing or treating a disease associated with immune enhancement or reduced immunity.

5 Claims, 7 Drawing Sheets

METHOD FOR PREPARING IRIDOID-RICH NONI FRUIT EXTRACT OR FRACTION THEREOF, METHOD FOR PREPARING IMMUNE-ENHANCING ACTIVE MATERIAL-RICH NONI FRUIT EXTRACT OR FRACTION THEREOF AND USE OF NONI FRUIT EXTRACT OR FRACTION THEREOF

CROSS REFERENCE TO RELATED APPLICATIONS

This application is a national stage application under 35 U.S.C. § 371 of International Application No. PCT/KR2020/007155, filed internationally on Jun. 2, 2020, which claims priority to Korean Patent Application No. 10-2019-0065431, filed Jun. 3, 2019, the contents of which are incorporated herein by reference in their entirety.

BACKGROUND

1. Field of the Invention

The present invention relates to a method of preparing a noni fruit extract containing a high iridoid content or a fraction thereof, a method of preparing a noni fruit extract containing a high content of an immune-enhancing active substance or a fraction thereof, and a use of a noni fruit extract or a fraction thereof, and more specifically, the present invention provides a method of preparing a noni fruit extract containing a high iridoid content or a fraction thereof, including preparing a noni fruit extract using ethanol in a specific concentration range as an extraction solvent, a method of preparing a noni fruit extract containing a high content of an immune-enhancing active substance or a fraction thereof, a pharmaceutical composition for enhancing immunity including the extract or a fraction thereof, a health functional food composition including the same constitution, a method of enhancing immunity using the extract or a fraction thereof, and a use of the extract or a fraction thereof in preparation of medicine for preventing or treating a disease associated with immune enhancement or reduced immunity.

2. Discussion of Related Art

Noni (*Morinda citrifolia* L.) is an evergreen shrub belonging to the family Rubiaceae and the genus Noni and includes an abundant amount of vitamins A and C, and it also contains bioactive substances such as flavonoids, iridoids, alkaloids and the like. In particular, South Pacific Polynesians (Tahiti natives) have used noni for edible and therapeutic purposes and functions for a long time, and even today, it is a tropical plant that is attracting attention as health food because it is used as a raw material for juice, raw food (powder) and the like.

Iridoid, which was discovered in 2009, is a unique plant chemical and a substance that is produced to defend itself from external environmental factors. It is mainly found in medicinal plants, and it is an ingredient that helps to enhance immune functions in skin aging, high blood pressure, diabetes and the like, and 19 types of the ingredient have been reported.

However, studies on how to efficiently extract iridoids from noni have been insufficient thus far.

As such, the present inventors have sought to discover a method of efficiently extracting deacetylasperulosidic acid (DAA), asperulosidic acid (ASPA) and asperuloside (ASP) among iridoid compounds from noni fruit, and when ethanol is used as an extraction solvent in a specific concentration range, a noni fruit extract containing a high content of the above three types of iridoid compounds can be prepared, and the present invention was completed by confirming that the extract or a fraction thereof prepared by the above method exhibited excellent efficacy in enhancing immunity.

Meanwhile, even though Korean Patent Publication No. 10-2009-0072555 discloses a method of preparing a concentrated solution of noni fruit, it merely suggests a method for effectively removing the unique taste or odor of noni, and there is no suggestion regarding a method of efficiently extracting the three types of iridoid compounds or immune-enhancing active substances from noni fruit.

SUMMARY OF THE INVENTION

An object of the present invention is to provide a method of efficiently extracting iridoids from noni.

Another object of the present invention is to provide a composition for enhancing immunity including a noni fruit extract or a fraction thereof.

Still another object of the present invention is to provide a method of enhancing immunity using a noni fruit extract or a fraction thereof.

Still another object of the present invention is to provide a use of a noni fruit extract or a fraction thereof in preparation of medicine for preventing or treating a disease associated with immune enhancement or reduced immune functions.

Still another object of the present invention is to provide a method of efficiently extracting an immune-enhancing active substance from noni.

In order to solve the above-mentioned problems, the present invention provides a method of preparing a noni fruit extract containing a high iridoid content or a fraction thereof including the following steps:

a) pulverizing noni fruit;

b) injecting 10 (w/w) % to 60 (w/w) % ethanol of 5 to 15 times the weight of the pulverized product into the pulverized product; and c) preparing an extract by extracting at 60° C. to 100° C. for 1 hour to 8 hours.

According to a preferred exemplary embodiment of the present invention, the ethanol in step b) may be 20 (w/w) % to 50 (w/w) % ethanol.

According to another preferred exemplary embodiment of the present invention, the extraction in step c) may be stirring extraction.

According to still another preferred exemplary embodiment of the present invention, the preparation method may further include d) filtering and concentrating the extract to prepare a concentrated solution.

According to still another preferred exemplary embodiment of the present invention, the iridoid may be one or more selected from the group consisting of deacetylasperulosidic acid (DAA), asperulosidic acid (ASPA) and asperuloside (ASP).

The present invention also provides a pharmaceutical composition and/or a health functional food composition for enhancing immunity including a noni fruit extract or a fraction thereof.

In addition, the present invention provides a method of enhancing immunity, including administering a noni fruit extract or a fraction thereof to a subject in need thereof at an effective amount.

The present invention also provides a use of a noni fruit extract or a fraction thereof in preparation of medicine for preventing or treating a disease associated with immune enhancement or reduced immunity.

According to a preferred exemplary embodiment of the present invention, the extract may be prepared by using 5 (w/w) % to 50 (w/w) % ethanol as an extraction solvent.

According to another preferred exemplary embodiment of the present invention, the fraction may be a purified water fraction of the 5 (w/w) % to 50 (w/w) % ethanol extract.

According to still another preferred exemplary embodiment of the present invention, the fraction may include a polysaccharide having a molecular weight of 10 kDa or more.

The present invention also provides a method of preparing a noni fruit extract containing a high content of an immune-enhancing active substance or a fraction thereof, including the following steps:

a) pulverizing noni fruit:

b) injecting 5 (w/w) % to 50 (w/w) % ethanol of 5 to 15 times the weight of the pulverized product into the pulverized product; and c) preparing an extract by extracting at 60° C. to 80° C. for 1 hour to 8 hours.

According to a preferred exemplary embodiment of the present invention, the preparation method may further include d) fractionating the obtained extract with purified water.

According to another preferred exemplary embodiment of the present invention, the immune-enhancing active substance may be an iridoid and a polysaccharide having a molecular weight of 10 kDa or more.

According to still another preferred exemplary embodiment of the present invention, the iridoid may be one or more selected from the group consisting of deacetylasperulosidic acid (DAA), asperulosidic acid (ASPA) and asperuloside (ASP).

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
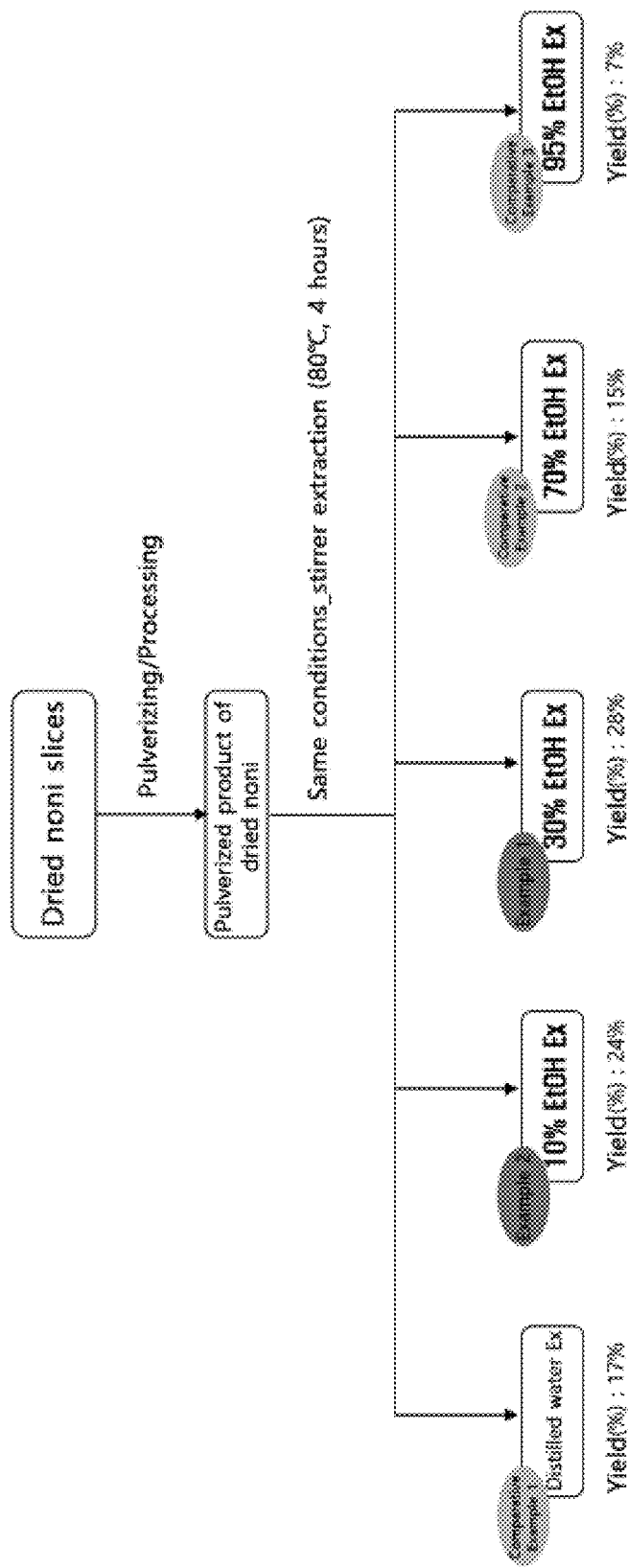
FIG. 1 is a schematic diagram showing the preparation method of a noni fruit extract of the present invention.

Hereinafter, exemplary embodiments of the present disclosure will be described in detail to be embodied by those skilled in the art. The present disclosure may be implemented in various forms and is not limited to the following embodiments.

As described above, the iridoid is known as a useful bioactive ingredient found in noni, but studies on how to efficiently extracting the above are insufficient.

As such, the present inventors have sought to develop a method of efficiently extracting deacetylasperulosidic acid (DAA), asperulosidic acid (ASPA) and asperuloside (ASP) among iridoid compounds from noni fruit, and when ethanol in a specific concentration range was used as an extraction solvent, a noni fruit extract containing a high content of the above three types of the iridoid compounds could be prepared, and the present invention was completed by confirming that the extract or a fraction thereof prepared by the above method exhibited excellent efficacy in immune enhancement.

Hereinafter, the present invention will be described in more detail.

The present invention provides a method of preparing a noni fruit extract containing a high iridoid content or a fraction thereof, including a) pulverizing noni fruit; b) injecting 10 (w/w) % to 95 (w/w) % ethanol of 5 to 15 times the weight of the pulverized product into the pulverized product; and c) preparing an extract by extracting at 60° C. to 80° C. for 1 hour to 8 hours.

As used herein, the term "extract" includes an extract solution obtained by extraction treatment of the noni fruit, more preferably, dried noni fruit, a diluted solution or a concentrated solution of the extract, a dried product obtained by drying the extract, a crude purification product or a purified product of the extract, or a mixture thereof and the like, and the extract itself and extracts of all formulations that can be formed by using the extract.

The noni fruit used in the preparation method of the present invention may be purchased commercially, or harvested or cultivated in nature, and noni fruit including all of the fruit flesh, peels and seeds dried by a natural or hot-air drying method is used.

The extract of the present invention may be extracted from natural, hybrid or variant plants of the respective plants, and it may be extracted from a plant tissue culture.

In the preparation method of the present invention, the method of extracting the extract is not particularly limited, and it may be extracted according to methods conventionally used in the art. Non-limiting examples of the extraction method include the hot water extraction method, ultrasonic extraction method, filtration method, reflux extraction method and the like, and these may be performed alone or in combination of two or more methods. In a specific exemplary embodiment of the present invention, extracts were prepared using stirring extraction.

In the preparation method of the present invention, the type of the extraction solvent used to extract the noni fruit is ethanol. Extraction using ethanol (that is, alcohol extraction) is not only the most environmentally friendly and economical extraction method for food processing, but also it was confirmed through the present invention that iridoids could be efficiently extracted compared to when other organic solvents such as methanol, hexane, ethyl acetate, methyl chloride or acetone were used as the extraction solvent.

In the preparation method of the present invention, the concentration of the ethanol in step b) may be 10 (w/w) % to 95 (w/w) %, more preferably, 10 (w/w) % to 60 (w/w) %, even more preferably, 20 (w/w) % to 60 (w/w) %, and most preferably, 20 (w/w) % to 50 (w/w) %.

In the preparation method of the present invention, a solvent extract may be prepared by extracting dried noni fruit at least once using the solvent, and after distilling the solvent extract under reduced pressure, a dried extract that is obtained by freeze drying or spray drying may be prepared.

Figure 2:
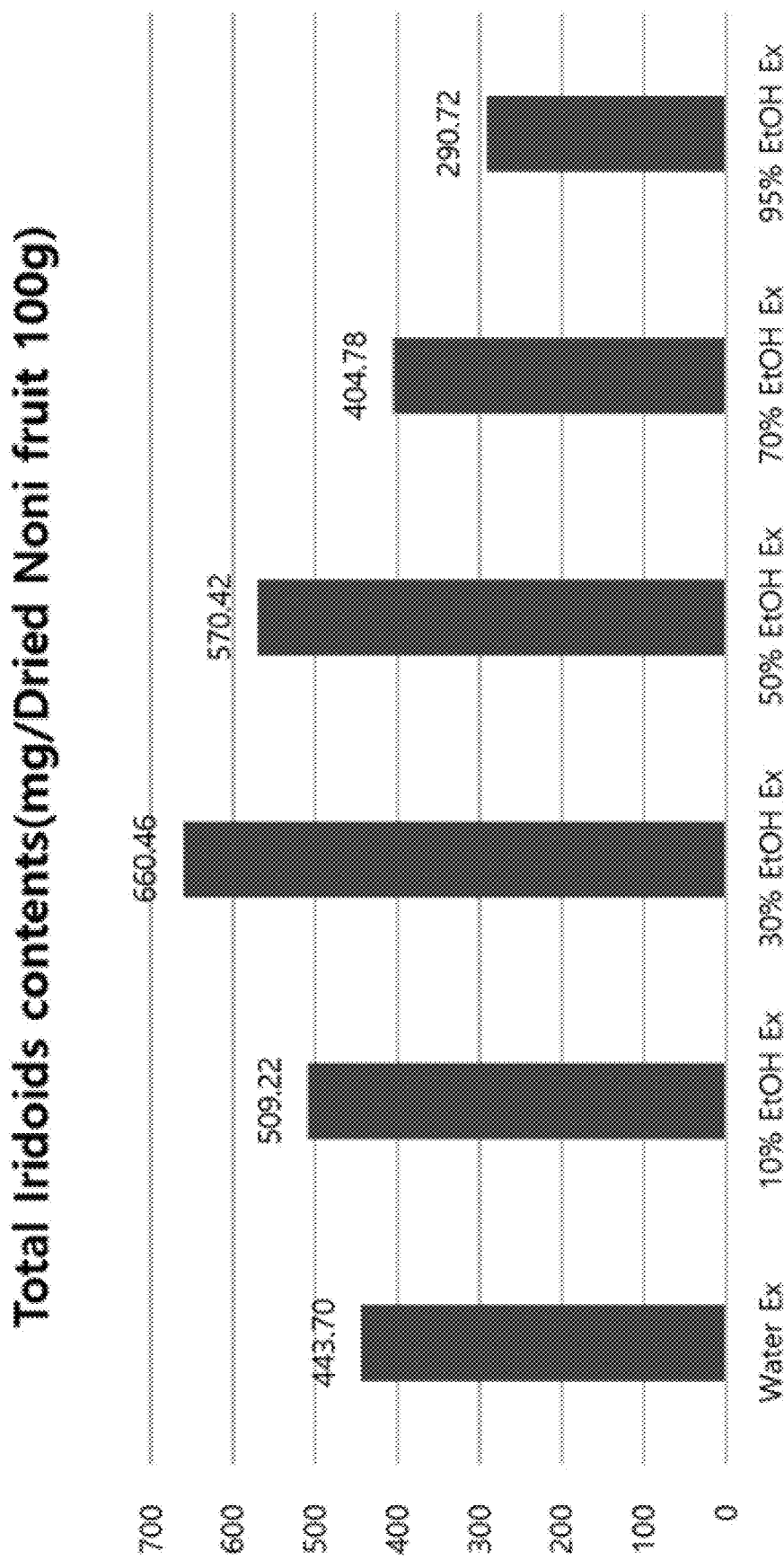
FIG. 2 is a graph showing the analysis of the total iridoid contents of noni fruit extracts depending on extraction solvents.
Figure 3:
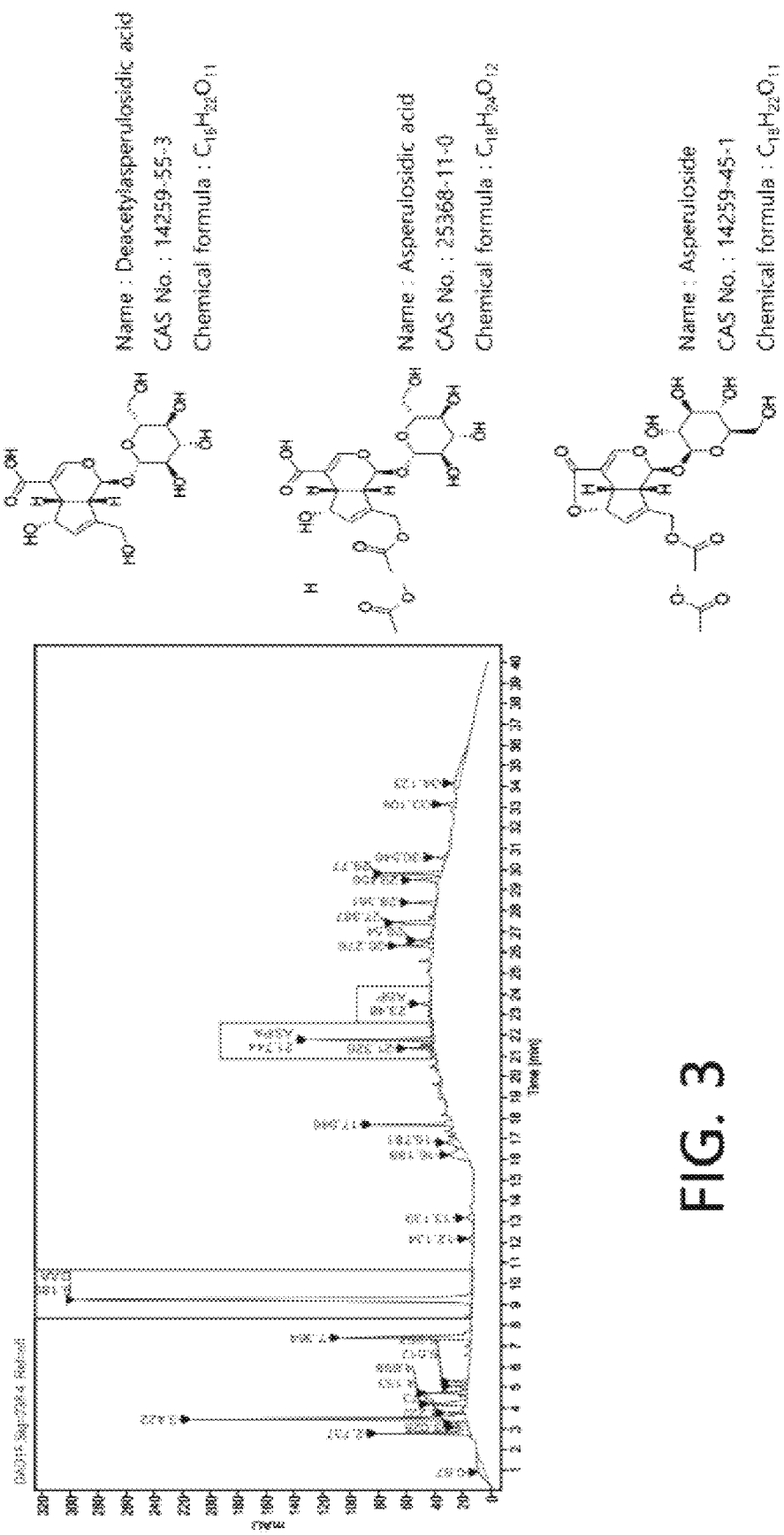
FIG. 3 shows the HPLC profile of a 30 (w/w) % ethanol noni fruit extract and information on three types of iridoid compounds (DAA, ASPA and ASP)

As shown in FIG. 1, the present inventors prepared noni fruit extracts using purified water, 10 (w/w) % ethanol, 30 (w/w) % ethanol, 50 (w/w) % ethanol, 70 (w/w) % ethanol and 95 (w/w) % ethanol as extraction solvents, respectively, and as shown in FIG. 2, it was confirmed that 10 (w/w) %, 30 (w/w) % and 50 (w/w) % ethanol solvent extracts showed high total iridoid contents among various solvent extracts. As a result of performing HPLC for the 30 (w/w) % ethanol extract which showed the highest total iridoid content among these solvent extracts, it was confirmed that deacetylasperulosidic acid (DAA), asperulosidic acid (ASPA) and asperuloside (ASP) were present as shown in FIG. 3.

Figure 4:
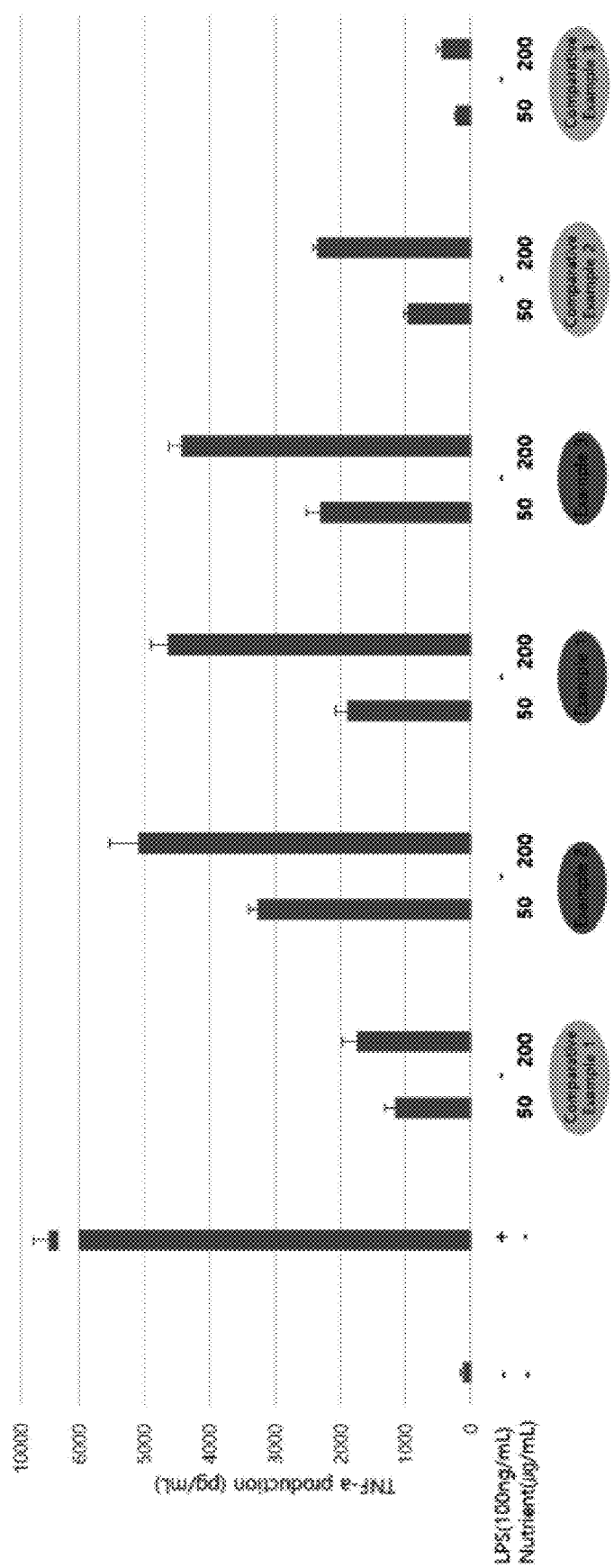
FIG. 4 is a graph showing the measurement of the TNF-α production amounts after treating macrophage cell line RAW264.7 with each solvent extract.

In order to confirm the immune-enhancing effect of each solvent extract prepared as described above, the present inventors treated each solvent extract to macrophage cell line RAW264.7 to determine the TNF-α production effect. As a result, as shown in FIG. 4, it was confirmed that excellent TNF-α production effect was shown in the 10 (w/w) %, 30 (w/w) % and 50 (w/w) % ethanol solvent extracts.

However, the TNF-α production effect of the 10 (w/w) % ethanol extract was superior to that of the 30(w/w) % ethanol extract, which showed the highest total iridoid content, and even though this shows that an excellent immune-enhancing effect is exhibited when the total iridoid content is high, it suggests that the total iridoid content and the immune-enhancing effect are not directly proportional.

As used herein, the term "fraction" refers to the result product obtained by performing fractionation to separate a specific component or a specific group of components from a mixture including several different constitutional components.

The fractionation method of obtaining the fraction in the present invention is not particularly limited, and may be performed according to a method conventionally used in the art. Non-limiting examples of the fractionation method may be, for example, a method of obtaining a fraction from the extract by treating a predetermined solvent to an extract obtained by extracting dried noni fruit.

In the present invention, the type of the solvent used to obtain the fraction is preferably purified water. In case of using a solvent other than purified water, the content of bioactive substances that exhibit immune-enhancing activity, including iridoids, may be drastically reduced so that the intended physiological activity may not appear.

Figure 5:
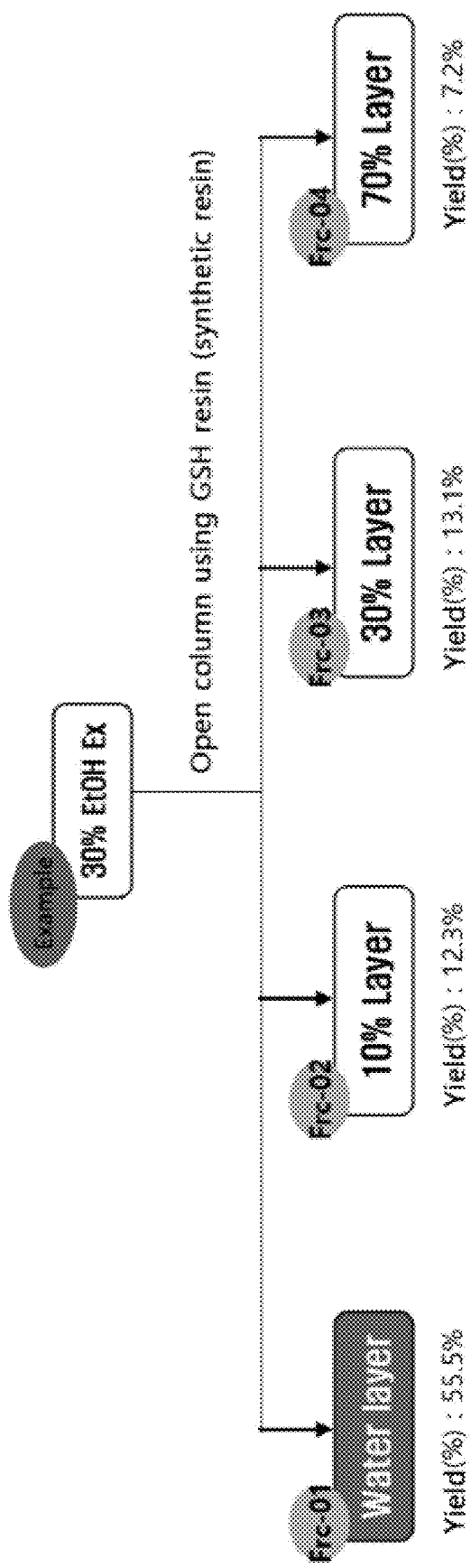
FIG. 5 is a schematic diagram showing the fraction preparation method of the noni fruit extract of the present invention.
Figure 6:
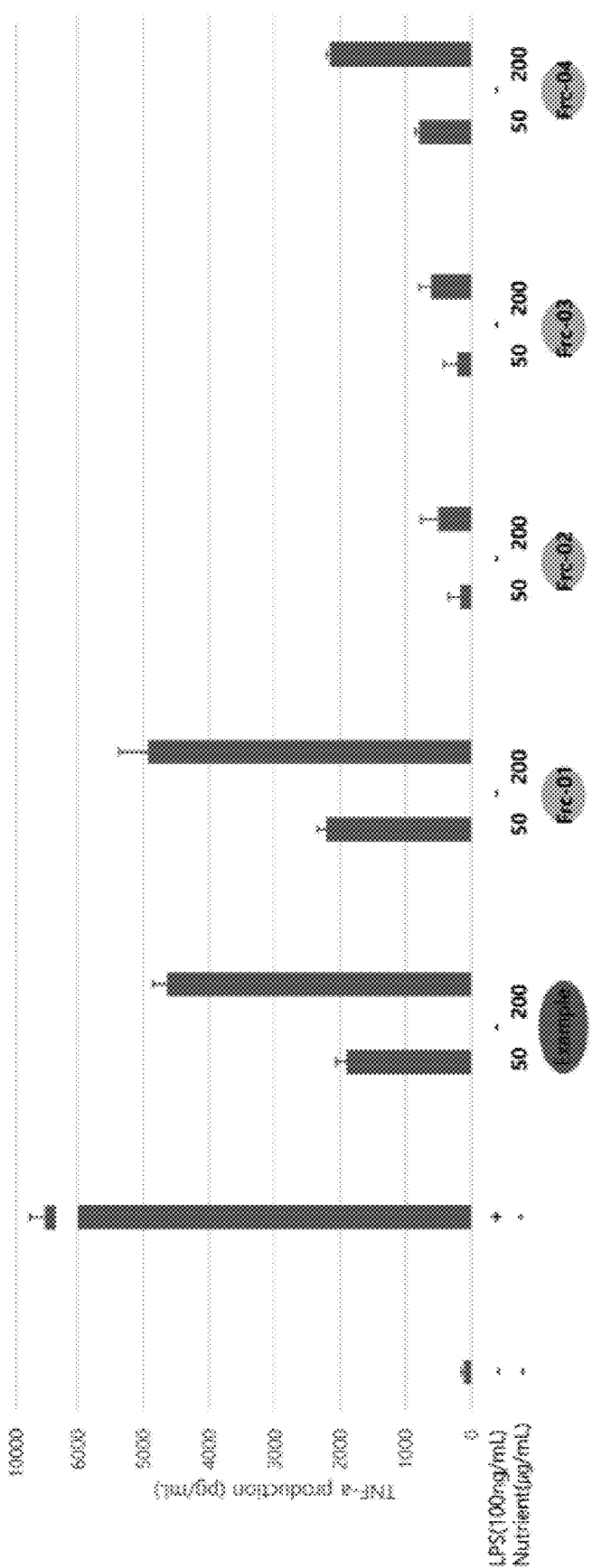
FIG. 6 is a graph showing the measurement of the TNF-α production amounts after treating macrophage cell line RAW264.7 with each fraction; and A) of FIG. 7 shows the GPC chromatography of pullulan used as a standard substance, and (B) shows the GPC chromatography of a purified water fraction (Frc-01).

In a specific exemplary embodiment of the present invention, as shown in FIG. 5, a noni fruit extract prepared using 30 (w/w) % ethanol as the extraction solvent was fractionated and purified in each section under the conditions of purified water, 10 (w/w) % ethanol, 30 (w/w) % ethanol and 70 (w/w) % ethanol, and macrophage cell line RAW264.7 was treated with each fraction to confirm the TNF-α production effect. As shown in FIG. 6, the TNF-α production effect of the fraction 1 (Frc-01), which is a purified water fraction, was the most excellent, and the same effect was found to be insignificant in other fractions.

Figure 7:
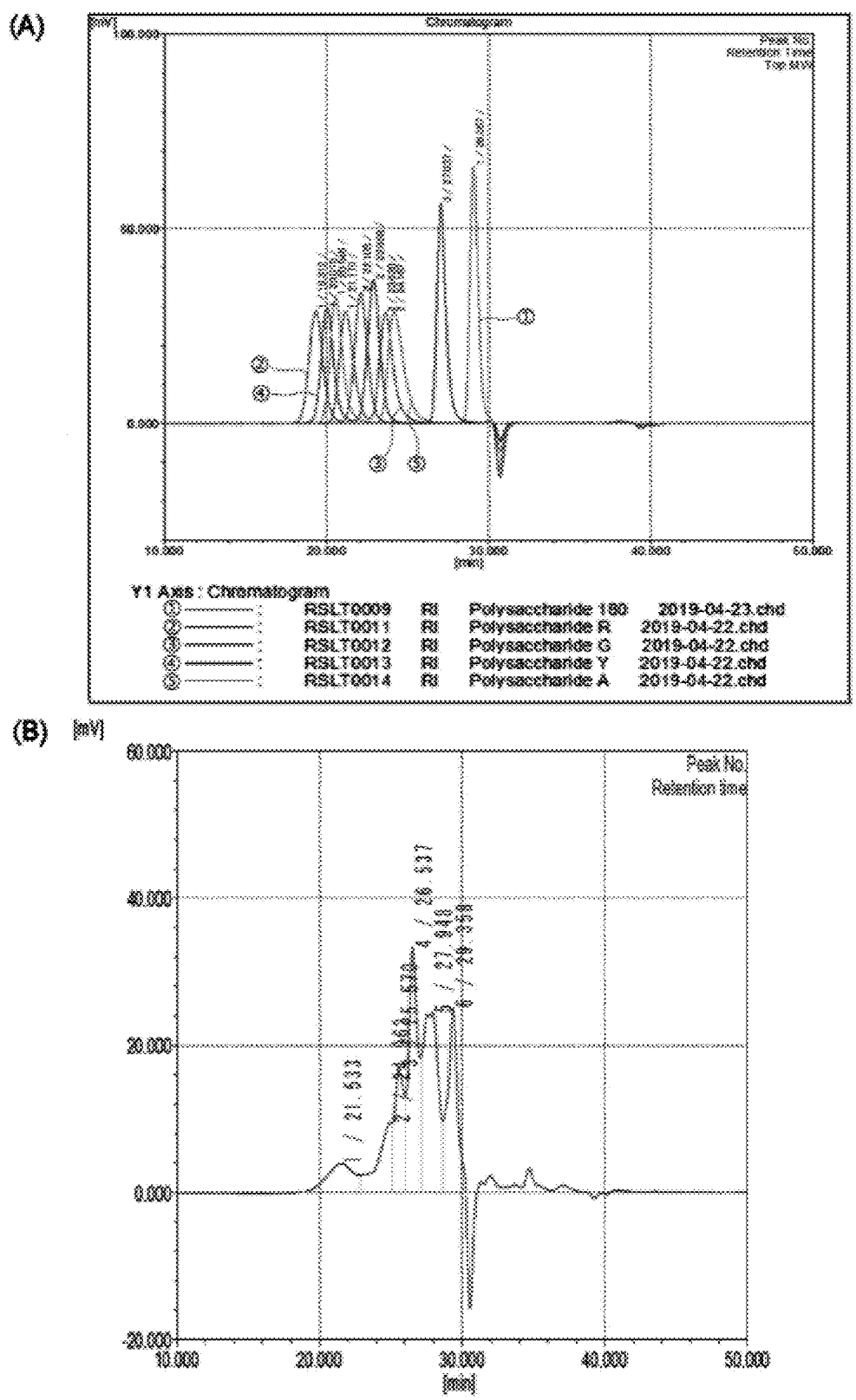

In addition, the present inventors performed a gel permeation chromatography (GPC) analysis to identify a substance substantially exhibiting immune-enhancing efficacy in the purified water fraction and determined its molecular weight. As shown in FIG. 7, it was confirmed that a polysaccharide having a molecular weight of 10 kDa or more was the substantially active ingredient exhibiting immune-enhancing efficacy.

Based on these results, when the TNF-α production effect shown in FIG. 4 is reinterpreted, while the 10 (w/w) % ethanol extract has a lower total iridoid content compared to the 30 (w/w) % and 50 (w/w) % ethanol extracts, it has a higher content of a polysaccharide having a molecular weight of 10 kDa or more compared to these extracts, and as a result, it can be interpreted to exhibit the most excellent immune-enhancing effect.

The present invention also provides a pharmaceutical composition and/or a health functional food composition for enhancing immunity, including a noni fruit extract containing a high iridoid content or a fraction thereof that is prepared by the above-mentioned preparation method.

In the pharmaceutical composition and/or health functional food composition of the present invention, a noni fruit extract or a fraction thereof may enhance both of the congenital and acquired immunities.

As confirmed in FIGS. 2 and 4, the total iridoid content and the immune-enhancing effect are not directly proportional, and as confirmed in FIG. 7, since the substance substantially exhibiting the immune-enhancing efficacy is a polysaccharide of 10 kDa or more, the composition of the present invention may be prepared by using ethanol in a concentration range different from the ethanol concentration used as the extraction solvent in the method of efficiently extracting iridoids.

Specifically, the composition for enhancing immunity of the present invention may include a noni fruit extract prepared by using 5 (w/w) % to 50 (w/w) % ethanol, more preferably, 5 (w/w) to 40 (w/w) ethanol, and most preferably, 5 (w/w) % to 30 (w/w) % ethanol as an extraction solvent.

In addition, the composition for enhancing immunity of the present invention may include a purified water fraction of the 5 (w/w) % to 50 (w/w) % ethanol noni fruit extract.

Specifically, the purified water fraction may be obtained by performing open column chromatography for concentrated solutions of the 5 (w/w) % to 50 (w/w) % ethanol noni fruit extracts by using purified water as an eluent, and in this case, the synthetic resin filled in the open column is preferably a hydrophobic synthetic resin.

As shown in FIG. 7, since it was confirmed that a polysaccharide having a molecular weight of 10 kDa or more in the purified water fraction was the substantially active ingredient exhibiting the immune-enhancing efficacy, the purified water fraction included in the composition for enhancing immunity of the present invention shows excellent immune-enhancing efficacy by having a polysaccharide having a molecular weight of 10 kDa or more as an active ingredient.

Based on the above results, additionally, the present invention provides a method of preparing a noni fruit extract containing a high content of an immune-enhancing active substance or a fraction thereof, including a) pulverizing noni fruit; b) injecting 5 (w/w) % to 50 (w/w) % ethanol of 5 to 15 times the weight of the pulverized product into the pulverized product; and c) preparing an extract by extracting at 60° C. to 80° C. for 1 hour to 8 hours.

The preparation method of a noni fruit extract containing a high content of an immune-enhancing active substance or a fraction thereof of the present invention may further include d) fractionating the obtained extract with purified water.

When other solvents are used besides purified water in the step d), the content of physiologically active substances exhibiting immune-enhancing activity, including iridoids, may be drastically reduced so that the intended physiological activity may not appear.

In the preparation method of a noni fruit extract containing a high content of an immune-enhancing active substance or a fraction thereof, the immune-enhancing active substance may be an iridoid and a polysaccharide having a molecular weight of 10 kDa or more, and the iridoid may be one or more selected from the group consisting of deacetylasperulosidic acid (DAA), asperulosidic acid (ASPA) and asperuloside (ASP).

In the preparation method of a noni fruit extract containing a high content of an immune-enhancing active substance or a fraction thereof of the present invention, the detailed description of each step is the same as the preparation method of a noni fruit extract containing a high iridoid content as described above except the concentration of ethanol used as the extraction solvent, and thus the description thereon is omitted.

In the preparation method, the concentration range of ethanol in which the immune-enhancing active substance can be extracted most efficiently may be 5 (w/w) % to 50 (w/w) %, preferably 5 (w/w) % to 40 (w/w) %, more preferably, 5 (w/w) % to 30 (w/w) %, and most preferably, 5 (w/w) % to 10 (w/w) %.

The pharmaceutical composition of the present invention may further include a pharmaceutically acceptable carrier.

The pharmaceutical composition of the present invention may be prepared in pharmaceutical formulations using methods well-known in the art to provide rapid, sustained or delayed release of the active ingredient after administering to a mammal. In the preparation of formulations, it is preferred that the active ingredient is mixed or diluted with a carrier or enclosed in a carrier in the form of a container.

Accordingly, the pharmaceutical composition of the present invention may be used by formulating in the form of oral dosage forms such as powders, granules, tablets, capsules, suspensions, emulsions, syrups, aerosols and the like, external preparations, suppositories and sterile injectable solutions, according to conventional methods. In addition, it may further include suitable carriers, excipients and diluents that are conventionally used in the preparation of compositions.

For example, examples of carriers that may be included in the pharmaceutical composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil and the like, but are not limited thereto. When formulated, diluents or excipients such as fillers, extenders, binders, wetting agents, disintegrating agents, surfactants and the like that are commonly used are used for preparation.

Examples of solid form preparations for oral administration include tablets, pills, powders, granules, capsules and the like, and in such solid form preparations, at least one excipient, for example, starch, calcium carbonate, sucrose or lactose, gelatin and the like are mixed in the compound for preparation. In addition to simple excipients, lubricants such as magnesium stearate and talc are also used.

Examples of oral liquid preparations may include suspensions, solvents, emulsions, syrups and the like, and may include various excipients such as wetting agents, sweeteners, fragrances, preservatives and the like, in addition to commonly used simple diluents such as water and liquid paraffin.

Examples of formulations for parenteral administration include sterilized aqueous solutions, non-aqueous solvents, suspensions, emulsions, lyophilized formulations and suppositories. As the non-aqueous solvent and suspending agent, propylene glycol, polyethylene glycol, vegetable oils such as olive oil, injectable esters such as ethyl oleate and the like may be used. As the base of suppositories, witepsol, macrogol, tween 61, cacao butter, laurin butter, glycerogelatin and the like may be used.

As used herein, the term "administration" means introducing the pharmaceutical composition of the present invention to patients in any suitable manner.

The mode of administration of the pharmaceutical composition according to the present invention is not particularly limited and may be in accordance with a method conventionally used in the art. The mode of administration is not limited as long as it can reach the target tissue and may be intraperitoneal administration, intravenous administration, intramuscular administration, subcutaneous administration, intradermal administration, oral administration, topical administration and intranasal administration. The pharmaceutical composition according to the present invention may be prepared in various formulations depending on the desired mode of administration.

The pharmaceutical composition of the present invention may be administered in a pharmaceutically effective amount.

The "pharmaceutically effective amount" refers to an amount sufficient to treat a disease at a reasonable benefit/risk ratio applicable to medical treatment, and the effective dose level may be determined by considering factors including the type and severity of a subject, age, gender, the type of virus infected, the activity of the drug, sensitivity to the drug, the time of administration, the route of administration and the rate of excretion, the duration of treatment, drugs used concurrently and other factors well-known in the medical field.

Conventional daily dosages of the pharmaceutical composition according to the present invention may be appropriately selected by those skilled in the art and may be administered once or divided into several times.

The composition of the present invention may be administered daily or intermittently, and the number of administrations per day may be administered once or divided into two or three times. In addition, the composition of the present invention may be used alone or in combination with other drug treatments for immune enhancement. In consideration of all of the above factors, it is important to administer an amount that can obtain the maximum effect in a minimum amount without side effects, and it can be easily decided by those skilled in the art.

The pharmaceutical composition of the present invention may be administered to a subject in need of immune enhancement to enhance immunity.

As used herein, the term "subject" refers to all animals, including humans, that have or are likely to develop metabolic diseases. In addition to humans, the animals may be mammals such as cows, horses, sheep, pigs, goats, camels, antelopes, dogs, cats and the like, which require treatment of similar symptoms, but are not limited thereto.

The health functional food composition of the present invention may include forms such as pills, powders, granules, infusions, tablets, capsules, liquids and the like, and foods to which the composition of the present invention may be added include, for example, various foods, for example, drinks, gums, teas, vitamin complexes, dietary supplements and the like.

There is no particular limitation on other ingredients that may be included in the health functional food composition of the present invention other than containing the noni fruit extract or a fraction thereof as an essential ingredient, and various herbal extracts, food supplement additives, natural carbohydrates or the like may be contained as additional components with conventional foods.

In addition, the food supplement additives include conventional food supplement additives in the art, for example, flavoring agents, flavors, coloring agents, fillers, stabilizers and the like.

Examples of the natural carbohydrates are monosaccharides, for example, glucose, fructose and the like; disaccharides, for example, maltose, sucrose and the like; and polysaccharides, for example, conventional sugar such as dextrin, cyclodextrin and the like, and sugar alcohol such as xylitol, sorbitol, erythritol and the like. Besides what is described above, for flavoring agents, natural flavoring agents (for example, rebaudioside A, glycyrrhizin and the like) and synthetic flavoring agents (saccharin, aspartame and the like) may be used advantageously.

In addition to the above, the health functional food composition of the present invention may contain a variety of nutritional supplements, vitamins, minerals (electrolytes), flavoring agents such as synthetic flavoring agents, natural flavoring agents and the like, coloring agents and fillers (cheese, chocolate and the like), pectic acid and a salt thereof, alginic acid and a salt thereof, organic acids, protective colloid thickeners, pH adjusters, stabilizers, preservatives, glycerin, alcohols, carbonation agents used in carbonated drinks and the like. Besides, it may contain pulp for the production of natural fruit juices, fruit juice drinks and vegetable drinks. These components may be used independently or in combination.

In the present invention, the health supplement food includes a health functional food, health food and the like.

The health functional food is the same term as food for special health use (FoSHU) and refers to foods that are processed to exhibit the bioregulatory function efficiently with high medical and medicinal effects in addition to nutrition supply. Here, the term "functional" means controlling nutrients for the structure and function of the human body or obtaining useful effects for health use such as physiological actions and the like. The food of the present invention may be prepared by a method that is conventionally used in the art, and upon preparation, raw materials and ingredients conventionally added in the art may be added for preparation. In addition, the formulation of the food may also be prepared without limitation as long as the formulation is recognized as a food. The health functional food composition of the present invention may be prepared in various forms of formulations, and unlike general medicine, it has an advantage that there is no side effect and the like that may occur while taken for a long term because food is the raw material.

The present invention also provides a method of enhancing immunity, including administering a noni fruit extract or a fraction thereof to a subject in need thereof at an effective amount.

In the immune-enhancing method of the present invention, since descriptions regarding the constitutions including the properties of a noni fruit extract or a fraction thereof, its effect and administration route, the number of administrations, administration amounts and the like are the same as described above, the description thereon is omitted.

In the immune-enhancing method of the present invention, the subject may be in a state of reduced immunity. For example, it may be in a state where various immune diseases such as asthma, seasonal or perennial rhinitis, allergic sinusitis, conjunctivitis, atopic dermatitis, urticaria, erythrocytosis of red blood cells, acute glomerulonephritis and the like may have occurred due to a decrease in immune function.

In the immune-enhancing method of the present invention, the noni fruit extract or a fraction thereof may be administered to a healthy subject having a normal immune function in terms of prevention of diseases associated with decreased immune functions.

The present invention also provides a use of a noni fruit extract or a fraction thereof in preparation of medicine for preventing or treating a disease associated with immune enhancement or reduced immunity.

Hereinafter, the present invention will be described in more detail with reference to examples. The following examples are only for illustrating the present invention, and it will be apparent to those skilled in the art that the scope of the present invention is not to be construed as being limited by these examples.

Example 1

Preparation of Noni Fruit Extract Using 30 (w/w) % Ethanol

After checking and screening for foreign substances and the like mixed in processed and dried noni fruit, the dried noni fruit was pulverized to 40 to 100 mesh in order to increase extraction efficiency. After adding 30 (w/w) % ethanol of 10 times the weight of the pulverized product into an extractor, the dried noni fruit extract, which is the raw material, was slowly introduced. After the injection of the raw material was completed, it was extracted with stirring at 80° C. for 4 hours. Afterwards, filtration was performed using Whatman No. 4 filter paper. The extract that was completely filtered was subjected to a reduced-pressure concentration process at 60° C. to 70° C. to prepare a concentrated solution and then was lyophilized to prepare a powder form (yield 28%).

Example 2

Preparation of Noni Fruit Extract Using 10 (w/w) % Ethanol

The noni extract was prepared in the same manner as in Example 1 above, except that 10 (w/w) % ethanol was used as the extraction solvent (yield 24%).

Example 3

Preparation of Noni Fruit Extract Using 50 (w/w) % Ethanol

The noni extract was prepared in the same manner as in Example 1 above, except that 50 (w/w) % ethanol was used as the extraction solvent (yield 21%).

Comparative Example 1

Preparation of Noni Fruit Extract Using Purified Water

The noni extract was prepared in the same manner as in Example 1 above, except that purified water was used as the extraction solvent (yield 17%).

Comparative Example 2

Preparation of Noni Fruit Extract Using 70 (w/w) % Ethanol

The noni extract was prepared in the same manner as in Example 1 above, except that 70 (w/w) % ethanol was used as the extraction solvent (yield 15%).

Comparative Example 3

Preparation of Noni Fruit Extract Using 95 (w/w) % Ethanol

The noni extract was prepared in the same manner as in Example 1 above, except that 95 (w/w) % ethanol was used as the extraction solvent (yield 7%).

The extraction solvents used in Examples 1 to 3 and Comparative Examples 1 to 3 are summarized and shown in Table 1.

TABLE 1

| Example/Comparative Example | Extraction solvent |
| --- | --- |
| Example 1 | 30 (w/w)% ethanol |
| Example 2 | 10 (w/w)% ethanol |
| Example 3 | 50 (w/w)% ethanol |
| Comparative Example 1 | Purified water |
| Comparative Example 2 | 70 (w/w)% ethanol |
| Comparative Example 3 | 95 (w/w)% ethanol |

Example 4

Analysis of Iridoid Content of Noni Fruit Extract

The iridoid content analysis was performed for each extract prepared through Examples 1 to 3 and Comparative Examples 1 to 3 above.

About 100 mg of each extract was collected in a 50 mL volumetric flask, and distilled water was added to the capacity line to be completely dissolved. The test solution filtered through a 0.45 μm syringe filter was used for analysis. The HPLC analysis method is shown in Table 2 below, the analyzed result values are shown in FIG. 2 by converting to the extraction yields of each Example and Comparative Example, and the HPLC profile of the extract of Example 1 is shown in FIG. 3.

TABLE 2

| Classification | Detailed content |
| --- | --- |
| Device | Agilient |
| Detector | UV (DAD) |
| Wavelength | 238 nm |
| Column | InfinityLab Poroshell 120 EC-C18 (150 × 4.6 mm, 5 μm) |
| Mobile phase | A: 0.1% formic acid dissolved in distilled water<br>B: 0.1% formic acid dissolved in acetonitrile |
| Flow rate | 0.5 mL/min |
| Injection volume | 10 μL |
| Oven temperature | 40° C. |
| Run-time | 40 minutes |

As shown in FIG. 2, the total iridoid contents of the noni fruit extracts of Examples 1 to 3 were significantly higher than those of the noni fruit extracts of Comparative Examples 1 to 3, and it was confirmed that the extract of Example 1 had the highest iridoid content among the above.

Example 5

Confirmation of Immune-Enhancing Effect of Noni Fruit Extract

In order to determine the immune-enhancing effect for each extract prepared through Examples 1 to 3 and Comparative Examples 1 to 3 above, the production of macrophage-derived TNF-α depending on extract treatment was measured in the present example. TNF is a cytokine that mediates and regulates innate immunity, and it is also secreted by antigen-stimulated T lymphocytes, NK cells and mast cells. Since activated macrophages are the main producing cells, the production of TNF was measured as a factor for analyzing the immune-enhancing effect.

Specifically, after the cultured mouse macrophage cell line RAW264.7 (KCLB #40071, Korean Cell Line Bank) was adjusted to a concentration of $1\times10^6$ cells/mL using RPMI1640 medium (Gibco, Cat #11875-093), it was inoculated in a 96-well plate and preincubated at 5% $CO_2$ and 37° C. for 18 hours. Afterwards, the medium was removed, and a medium was treated that contained each extract at a concentration of 50 μg/mL and 200 μg/mL, respectively and cultured. After 24 hours, the supernatant was transferred to another 96-well plate by 100 μL, the TNF-α concentration was measured according to the manufacturer's instructions using mouse TNF-α enzyme-linked immunosorbent assay (ELISA) kit (Cat #MTA00B) from R&D Systems, and the result was shown in FIG. 4.

As confirmed in FIG. 4, the noni fruit extracts of Examples 1 to 3 showed more excellent TNF-α production effects than the noni fruit extracts of Comparative Examples 1 to 3, and the 10 (w/w) % noni extract of Example 2 showed the most excellent TNF-α production effect among these.

Example 6

Confirmation of Active Substance of Noni Fruit Extract 6-1. Preparation of Fraction of Noni Fruit Extract Since it was confirmed that the 30 (w/w) % ethanol noni fruit extract of Example 1 exhibited an excellent immune-enhancing effect and contained the highest total content of iridoids, additional fractions were prepared and screened to confirm the clear active ingredients for the above.

Specifically, as shown in FIG. 5, the 30 (w/w) % ethanol noni fruit extract of Example 1 was injected into an open column filled with TRILITE® GSH-20 resin (hydrophobic synthetic resin), and the 30 (w/w) % ethanol noni fruit extract of Example 1 was fractionated and purified in each section under the condition of purified water, 10 (w/w) % ethanol, 30 (w/w) % ethanol and 70 (w/w) % ethanol as eluates. The immune-enhancing activity for each fraction (fractionation) was confirmed by the same method as in Example 4, and the results are shown in FIG. 6.

As confirmed in FIG. 6, the immune-enhancing effect of the fraction 1 (Frc-01), which is a purified water fraction, was shown to be the highest, and it was confirmed that the immune-enhancing effect was insignificant in other fractions. Through this, it can be seen that the hydrophilic substrate exhibits an immune-enhancing effect at a higher portion.

6-2. GPC Analysis of Purified Water Fraction

In order to measure the molecular weight of a substance that substantially exhibits efficacy in the purified water fraction (Frc-01) exhibiting immune-enhancing efficacy, gel permeation chromatography (GPC) analysis was performed. Table 3 shows the analysis conditions, (A) of FIG. 7 shows the GPC analysis performance result of pullulan used as a standard substance, and (B) shows the GPC analysis performance result of the purified water fraction (Frc-01).

TABLE 3

| Classification | Detailed content |
| --- | --- |
| Device | Tosh Co. EcoSEC HLC-8320 GPC |
| Detector | RI-Detector |
| Column | 2XTSKgel GMPWxl + TSKgel G2500PWxl (7.8 × 300 mm) |
| Mobile phase | 0.1M NaNO$_3$ |
| Flow rate | 1.0 mL/min |
| Injection volume | 100 µL, 3 mg/mL |
| Oven temperature | 40° C. |

As a result of the GPC analysis, it was confirmed that the purified water fraction included polysaccharides whose average molecular weight is about 10 kDa or more, and these polysaccharides were the substantially active ingredients exhibiting the immune-enhancing efficacy.

In the preparation method of a noni fruit extract containing a high iridoid content and the preparation method of a noni fruit extract containing a high content of an immune-enhancing active substance of the present invention, ethanol in a specific concentration range is used as an extraction solvent, and it is possible to efficiently extract 3 types of iridoid compounds (DAA, ASPA and ASP) from noni fruit. Since ethanol is used as the extraction solvent, it is the most environmentally friendly and economical food processing. In addition, the immune-enhancing composition of the present invention contains a high concentration of a polysaccharide having a molecular weight of 10 kDa or more, which is a substantially active substance, thereby exhibiting excellent efficacy in enhancing immunity.

Hereinafter, the present invention will be described in more detail through examples. However, since various changes can be applied to the present invention and the present invention has various forms, specific examples and descriptions described below are only for helping to understand of the present invention. However, it is not intended to limit the present invention to any particular form of disclosure. It is to be understood that the scope of the present invention includes all modifications, equivalents and substitutes included in the scope of the spirit and technological field of the present invention.

What is claimed is:

1. A method of enhancing immunity, comprising administering a noni fruit extract or a purified water fraction thereof to a subject in need thereof at an effective amount, wherein the extract is prepared by using 10 (w/w) % ethanol as an extraction solvent, and the ethanol extract and the purified water fraction thereof comprise a polysaccharide having a mean molecular weight of 10 kDa or more.

2. The method of claim 1, wherein the extract is prepared by the following steps of:
    a) pulverizing noni fruit;
    b) injecting 10 (w/w) % ethanol of 5 to 15 times the weight of the pulverized product into the pulverized product; and
    c) preparing an extract by extracting at 60° C. to 80° C. for 1 hour to 8 hours.

3. The method of claim 1, wherein the fraction is prepared by the following steps of:
    a) pulverizing noni fruit;
    b) injecting 10 (w/w) % ethanol of 5 to 15 times the weight of the pulverized product into the pulverized product;
    c) preparing an extract by extracting at 60° C. to 80° C. for 1 hour to 8 hours; and
    d) fractionating the obtained extract with purified water.

4. The method of claim 1, wherein an immune enhancing active substance of the noni fruit extract or the fraction thereof is an iridoid and a polysaccharide having a molecular weight of 10 kDa or more.

5. The method of claim 4, wherein the iridoid is one or more selected from the group consisting of deacetylasperulosidic acid (DAA), asperulosidic acid (ASPA) and asperuloside (ASP).

* * * * *